United States Patent
Ouchi et al.

(10) Patent No.: US 7,166,301 B1
(45) Date of Patent: Jan. 23, 2007

(54) IMMEDIATE RELEASE MEDICINAL COMPOSITIONS FOR ORAL USE

(75) Inventors: Kiyohisa Ouchi, Nagano (JP); Kaoru Kaneko, Tokyo (JP); Ken Kanada, Nagano (JP)

(73) Assignee: Kissei Pharmaceutical Co., Ltd., Nagano (JP)

(*) Notice: Subject to any disclaimer, the term of this patent is extended or adjusted under 35 U.S.C. 154(b) by 0 days.

(21) Appl. No.: 09/979,149

(22) PCT Filed: May 21, 1999

(86) PCT No.: PCT/JP99/02669

§ 371 (c)(1),
(2), (4) Date: Dec. 26, 2001

(87) PCT Pub. No.: WO00/71117

PCT Pub. Date: Nov. 30, 2000

(51) Int. Cl.
*A61K 9/22* (2006.01)
*A61K 9/20* (2006.01)

(52) U.S. Cl. ............... 424/468; 424/464; 424/469
(58) Field of Classification Search ............ 424/489, 424/273, 451, 457, 424–428, 464–468
See application file for complete search history.

(56) References Cited

U.S. PATENT DOCUMENTS

| | | | |
|---|---|---|---|
| 3,818,096 A * | 6/1974 | Sherlock | 424/273 |
| 4,916,163 A | 4/1990 | Ni | |
| 5,202,335 A * | 4/1993 | Sato et al. | 514/307 |
| 5,258,185 A * | 11/1993 | Bauer et al. | 424/484 |
| 6,071,539 A * | 6/2000 | Robinson et al. | 424/466 |

(Continued)

FOREIGN PATENT DOCUMENTS

| | | |
|---|---|---|
| EP | 0 507 534 A1 | 10/1992 |
| JP | 63-115815 (A) | 5/1988 |
| JP | 05-139973 | 6/1993 |
| JP | 5-139973 (A) | 6/1993 |

(Continued)

OTHER PUBLICATIONS

Ohnota et al, Novel Rapid and Short Acting hypoglycemic Agent, a Calcium(2s)-2-benzyl-3-(cis-hexahydro-2isoindolinylcarbonyl) Propionate (KAD-1229) . . . Journal of Pharmacology and Experimental Therapeutics, 1994, vol. 269, vo. 2, pp. 489-495.*

(Continued)

*Primary Examiner*—Michael G. Hartley
*Assistant Examiner*—Micah-Paul Young
(74) *Attorney, Agent, or Firm*—Sughrue Mion, PLLC

(57) ABSTRACT

The present invention relates to an immediate release oral pharmaceutical composition which comprises as an active ingredient calcium salt of a benzylsuccinic acid derivative represented by the formula:

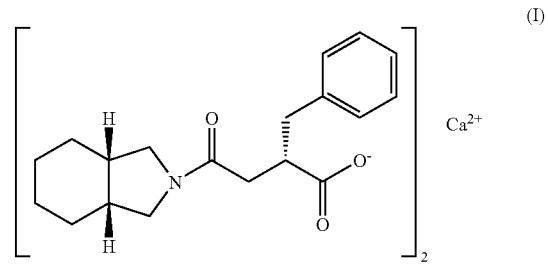

or its hydrate, which is useful as an agent for the treatment of diabetes.

5 Claims, 2 Drawing Sheets

U.S. PATENT DOCUMENTS 6,075,024 A * 6/2000 Young et al. .......... 514/253.08
6,165,512 A * 12/2000 Mezaache et al. .......... 424/489

FOREIGN PATENT DOCUMENTS

| JP | 07-076516 | 3/1995 |
| JP | 7-76516 (A) | 3/1995 |
| WO | WO 88/03023 A1 | 5/1988 |

OTHER PUBLICATIONS

Ohnota et al, Novel Rapid and Short-Acting Hypoglycemic Agent . . . , The Journal of Pharmacology and Experimental Therapeutics, 1994, vol. 269, No. 2, pp. 489-495.*

Ohnota et al; The Journal of Pharmacology and Experimental Therapeutics, 1994, vol. 269, No. 2, pp. 489-495.*

Kikuchi Masatoshi, Sogo Rinsho, (1996), 45(12), p. 2765-2771.

Ohnota Hideki et al., Jpn. J. Pharmacol., (1996), 71(4), p. 315-23.

Kinukawa Mayumi et al., Br. J. Pharmacol., (1996), 117(8), p. 1702-6.

Ohnota Hideki et al., Can. J. Physiol. Pharmacol., (1995), 73(1), p. 1-6.

Ohnota Hideki et al., J. Pharmacol. Exp. Ther., (1994), 269(2), p. 489-95.

The Japanese Phamacopocia, Fourteenth Edition, pp. 31-33; Apr. 1, 2001.

* cited by examiner

IMMEDIATE RELEASE MEDICINAL COMPOSITIONS FOR ORAL USE

TECHNICAL FIELD

The present invention relates to an immediate release oral pharmaceutical composition useful as an agent for the treatment of diabetes.

BACKGROUND OF THE INVENTION

Calcium salt of a benzylsuccinic acid derivative (chemical name: (2S)-2-benzyl-3-(cis-hexahydro-2-iso-indolinylcarbonyl)propionic acid) represented by the formula:

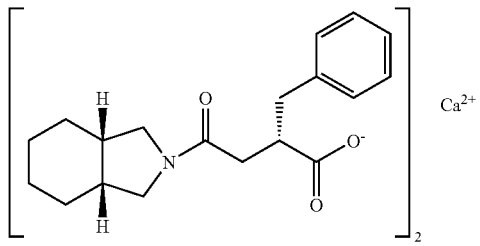

or its hydrate, which is an active ingredient in the pharmaceutical composition of the present invention, has a remarkable lowering action of blood sugar and has been known as a compound useful as an agent for the treatment of diabetes (Japanese Patent Laid-Open-No. 356459/1992).

Sulfonylurea agents (SU agents) such as glibenclamide, gliclazide and the like which have been frequently used for the treatment of diabetes take long to exert their effects and have persisting effects for several hours, so that it has been pointed out a problem that a risk of hypoglycemic symptoms increases conversely. For example, when SU agent is taken at a dose of sufficiently suppressing postprandial hyperglycemia, a problem that hypoglycemia is caused between meals can not be avoided. However, since effects of the present compound are shortly persistent, it is expected as a therapeutic agent for hyperglycemia which corrects only postprandial hyperglycemic condition without causing hypoglycemic condition between meals.

Rapid absorption after taking a drug in addition to early excretion of an active component from blood is required to correct only postprandial hyperglycemic condition without causing hypoglycemic condition between meals. Thus, development of immediate release preparations is needed in postprandial hyperglycemia treatment, wherein disintegration of the pharmaceutical composition and dissolution of the active ingredient are excellent. Generally, it is necessary for immediate release preparations to usually have an ability of about 75% or more drug release (drug dissolution) within 20 minutes after taking the drug (Iyakuhin no Kaihatsu [Development of medicines] Vol. 11, pp. 65–77, published by Hirokawa Shoten). It is concerned that the present compound is problematic in dissolution since it is poorly soluble in water. Therefore, in order to solve the problem, early development of excellent immediate release preparations has been greatly desired.

DISCLOSURE OF THE INVENTION

The present invention relates to an immediate release oral pharmaceutical composition which comprises as an active ingredient calcium salt of a benzylsuccinic acid derivative represented by the formula:

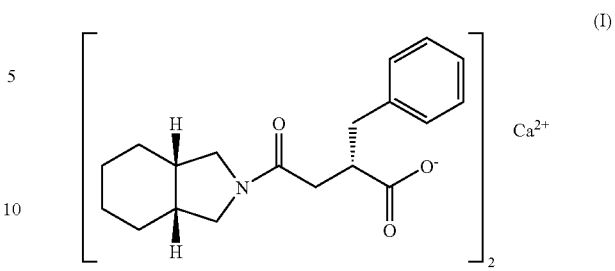

or its hydrate.

The invention relates to an immediate release oral pharmaceutical composition which comprises as an active ingredient calcium salt of the benzylsuccinic acid derivative represented by the above formula (I) or its hydrate, characterized by comprising at least silicon dioxide.

The invention relates to an immediate release oral pharmaceutical composition which comprises as an active ingredient calcium salt of the benzylsuccinic acid derivative represented by the above formula (I) or its hydrate, characterized by comprising at least partly pregelatinized starch.

BEST MODE FOR CARRYING OUT THE INVENTION

Figure 1:
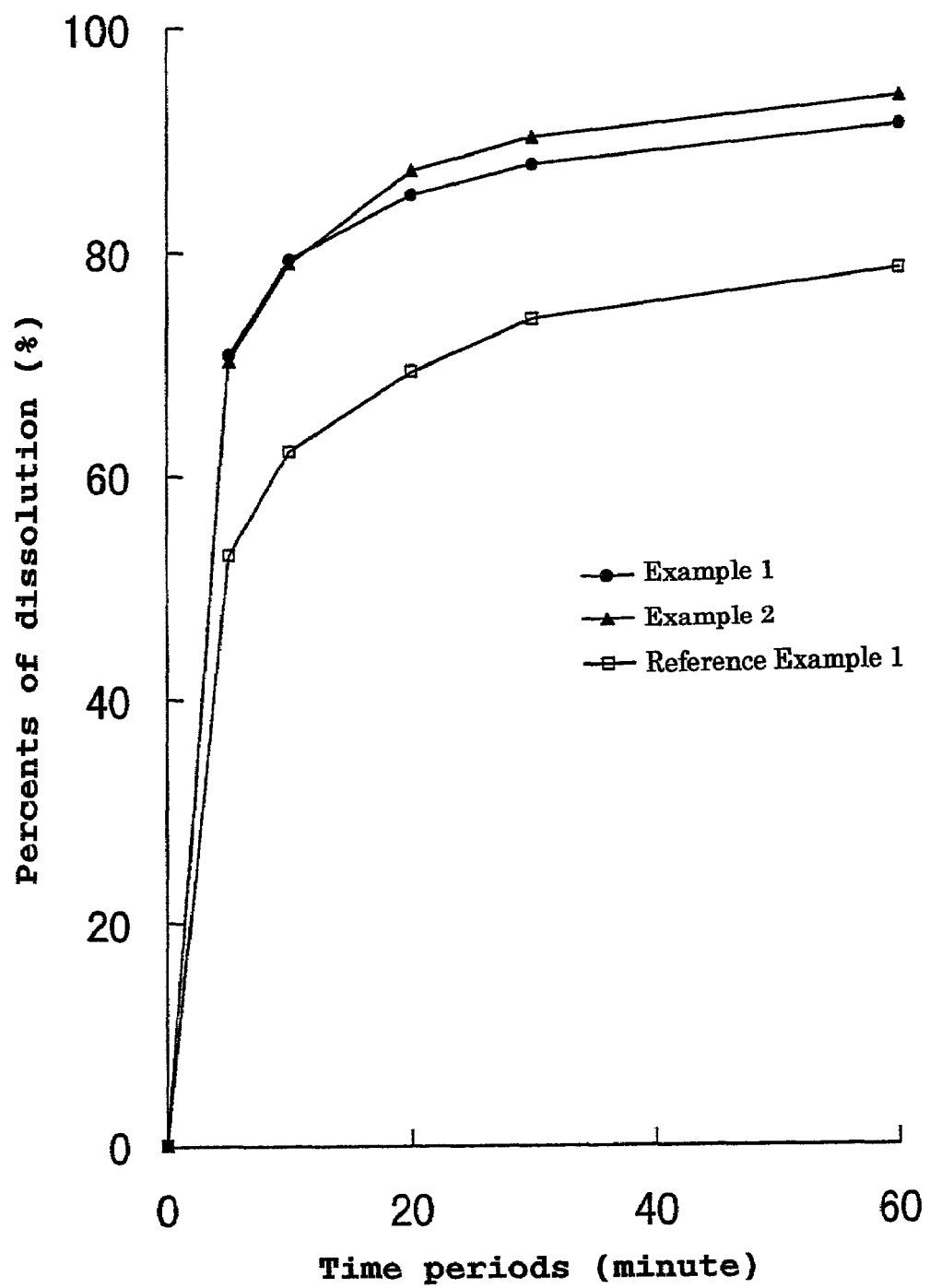
FIG. 1 is a graph showing a dissolution of various tablets described in Examples 1 and 2 and in Reference Example 1 in which dihydrate of calcium salt of the benzylsuccinic acid derivative of the above formula (I) is an active ingredient. The vertical and the horizontal axes denote percents of dissolution (%) of the active ingredient and time periods (minute) passed after the start of the tests, respectively.

The present inventors have intensively studied to find immediate release oral pharmaceutical compositions comprising as an active ingredient calcium salt of the benzylsuccinic acid derivative represented by the above formula (I) or its hydrate, which have excellent disintegration and dissolution and are therefore useful as agents for the treatment of diabetes. As a result, it was advantageously found that pharmaceutical compositions prepared by adding at least silicon dioxide or partly pregelatinized starch thereto enhance the disintegration and improve remarkably the dissolution, and thereby the present invention has been completed.

In immediate release oral pharmaceutical compositions comprising an active ingredient calcium salt of the benzylsuccinic acid derivative represented by the above formula (I) or its hydrate, even when tablets are prepared according to a dry method (direct compressing method), by which good disintegration is generally obtained, using disintegrants usually used such as sodium carboxymethyl starch and low substituted hydroxypropylcellulose, no preparations having good dissolution were obtained. The preparations obtained delayed the dissolution and have abnormally low percentages of dissolution. However, when the tablets were prepared by adding silicon dioxide, which is usually used as a lubricant, extremely excellent dissolution was surprisingly observed. For example, rapid dissolution was observed just after the start of the dissolution test using first fluid of the Japanese Pharmacopoeia, and a maximum dissolution rate was also extremely high.

Moreover, even when the tablets were prepared according to a wet method (wet granule-compressing method), which is generally inferior in disintegration, the silicon dioxide-added preparation exhibited surprisingly higher dissolution efficiency compared to the preparations in which sodium carboxymethyl starch or low substituted hydroxypropylcellulose, which is usually used as a disintegrant, was added. For example, rapid dissolution was observed just after the start of the dissolution test using first fluid of the Japanese Pharmacopoeia, and a maximum dissolution rate was also extremely high. Furthermore, when tablets were prepared according to the wet methods, the tablets in which sodium carboxymethyl starch or low substituted hydroxypropylcellulose, which is usually used as a disintegrant, was added were not satisfied because the dissolution rates were still low even after considerable time periods passed, and particular differences were observed in dissolution. On the contrary, when tablets were prepared according to the wet method employing the addition of partly pregelatinized starch as a disintegrant, good dissolution was observed as in the case with the addition of silicon dioxide. The preparation in which carmellose was added as a disintegrant exhibited high dissolution efficiency as well as the pharmaceutical composition of the present invention, but it turned the color of the preparation into pale yellow due to incompatible combination with the calcium salt of the benzylsuccinic acid derivative represented by the above formula (I) as the active ingredient. In addition, it was undesirable because its stability is not good due to decomposition of the active ingredient.

That is, the present invention relates to an immediate release oral pharmaceutical composition which comprises as an active ingredient calcium salt of the benzylsuccinic acid derivative represented by the above formula (I) or its hydrate, characterized by comprising at least silicon dioxide or partly pregelatinized starch, wherein it has remarkable disintegration and dissolution of the active ingredient without incompatible combination with calcium salt of the benzylsuccinic acid derivative represented by the above formula (I) and is excellent in a long term storage.

The calcium salt of the benzylsuccinic acid derivative represented by the above formula (I) or its hydrate comprising as an active ingredient in the present invention can be prepared by the methods described in the references, similar methods thereto or the like (for example, Japanese Patent Laid-Open No. 356459/1992).

Examples of silicon dioxide used for the present invention can include, but are not limited to, light anhydrous silicic acid, hydrated silicon dioxide and the like. The amount of silicon dioxide to be added is not limited but the blending from 0.5 to 5% by weight based on the whole preparation is sufficient.

As partly pregelatinized starch used for the present invention, various degrees of pregelatinized starch can be used. For example, such partly pregelatinized starches include a commercially available partly pregelatinized starch [PCS (trademark)]. The amount of partly gelatinized starch to be added is not limited but the blending from 5 to 20% by weight based on the whole preparation is sufficient.

The oral pharmaceutical compositions of the present invention can apply for various formulations, and typical formulations can include granules, fine granules, powders, tablets and capsules.

For example, granules, fine granules and powders can be prepared by conventional methods. Tablets can be prepared using granules or fine granules by conventional methods, or by directly granulating according to a dry method (direct compressing method) by conventional methods. Capsules can be prepared by directly filling granules, fine granules or mixed powders in the capsules by conventional methods.

When the pharmaceutical compositions of the present invention are prepared, suitable additives for each preparation such as diluents, binders, surfactants, lubricants, glidants, coating materials, plasticizers, coloring agents, flavoring agents and the like can be further used as occasion demands. These additives are those which are usually used pharmaceutically, and any of them can be used so long as they do not affect adversely on dissolution of and combination with the calcium salt of the benzylsuccinic acid derivative represented by the above formula (I) or its hydrate.

Diluents can include, for example, cellulose or cellulose derivatives such as microcrystalline cellulose and the like; starch or starch derivatives such as corn starch, wheat starch, cyclodextrin and the like; sugar or sugar alcohol such as lactose, D-mannitol and the like; and inorganic diluents such as dried aluminum hydroxide gel, precipitated calcium carbonate, magnesium aluminometasilicate, dibasic calcium phosphate and the like.

Binders can include, for example, hydroxypropylcellulose, methylcellulose, hydroxypropylmethylcellulose, povidone, dextrin, pullulane, hydroxypropyl starch, polyvinyl alcohol, scacia, agar, gelatin, tragacanth, macrogol and the like.

Surfactants can include, for example, sucrose esters of fatty acids, polyoxyl stearate, polyoxyethylene hydrogenated castor oil, polyoxyethylene polyoxypropylene glycol, sorbitan sesquioleate, sorbitan trioleate, sorbitan monostearate, sorbitan monopalmitate, sorbitan monolaurate, polysorbate, glyceryl monostearate, sodium lauryl sulfate, lauromacrogol and the like.

Lubricants can include, for example, stearic acid, calcium stearate, magnesium stearate, talc and the like.

Glidants can include, for example, dried aluminium hydroxide gel, magnesium silicate and the like.

Coating materials can include, for example, hydroxypropylmethylcellulose 2910, aminoalkyl methacrylate copolymer E, polyvinylacetal diethylaminoacetate, macrogol 6000, titanium oxide and the like.

Plasticizers can include, for example, triethyl citrate, triacetin, macrogol 6000 and the like.

The pharmaceutical compositions of the present invention are extremely stable, since neither change in its appearance and dissolution rate nor decomposition of its active ingredient is observed even after placing for 1 week under a severe condition of high temperature and humidity.

The contents of the present invention are further described in detail by the following Reference Examples, Examples and Test Examples, but the present invention is not limited thereto.

REFERENCE EXAMPLE 1

| | |
|---|---|
| Active component | 5.0 mg |
| Microcrystalline cellulose | 27.5 mg |
| Lactose | 28.7 mg |
| Corn starch | 10.0 mg |
| Low substituted hydroxypropylcellulose | 3.0 mg |
| Calcium stearate | 0.8 mg |
| [Total] | 75.0 mg |

After 412.5 g of microcrystalline cellulose, 430.5 g of lactose, 150.0 g of corn starch, 45.0 g of low substituted hydroxypropylcellulose (brand name: L-HPC/LH-11, produced by Shin-Etsu Chemical Co., Ltd.) and 12.0 g of calcium stearate were mixed with 75.0 g of dihydrate of calcium salt of the benzylsuccinic acid derivative represented by the formula (I) (active component), the mixture was compressed with a pressure of 700 kg using 6 mm diameter round-faced (5 R) punch to prepare tablets of the above composition.

REFERENCE EXAMPLE 2

| | |
|---|---|
| Active component | 22.0 mg |
| Lactose | 56.0 mg |
| Corn starch | 24.0 mg |
| Microcrystalline cellulose | 13.2 mg |
| Carmellose | 8.0 mg |
| Hydroxypropylcellulose | 2.4 mg |
| Calcium stearate | 1.2 mg |
| [Total] | 126.8 mg |

After 5.6 g of lactose, 2.4 g of corn starch, 1.32 g of microcrystalline cellulose and 0.8 g of carmellose (brand name; NS-300 (trademark), produced by Gotoku Yakuhin Co., Ltd.) were mixed with 2.2 g of dihydrate of calcium salt of the benzylsuccinic acid derivative represented by the formula (I) (active component), 4 g of an aqueous solution of 6% by weight of hydroxypropylcellulose (0.24 g as hydroxypropylcellulose) was added thereto. The mixture was granulated in a mortar, and the granules were passed through screen after drying in a shell dryer to yield granules of 30 mesh (500 μm) or less. Calcium stearate was mixed to the granules to be at 0.95%, and the mixture was compressed with a pressure of 500 kg using 7 mm diameter round-faced (9.5 R) punch to prepare tablets of the above composition.

REFERENCE EXAMPLE 3

| | |
|---|---|
| Active component | 22.0 mg |
| Lactose | 56.0 mg |
| Corn starch | 24.0 mg |
| Microcrystalline cellulose | 13.2 mg |
| Sodium carboxymethyl starch | 8.0 mg |
| Hydroxypropylcellulose | 2.4 mg |
| Calcium stearate | 1.2 mg |
| [Total] | 126.8 mg |

After 5.6 g of lactose, 2.4 g of corn starch, 1.32 g of microcrystalline cellulose and 0.8 g of sodium carboxymethyl cellulose (brand name: Primogel [trademark], produced by Matsutani Chemical Co., Ltd.) were mixed with 2.2 g of dihydrate of calcium salt of the benzylsuccinic acid derivative represented by the formula (I) (active component), 4 g of an aqueous solution of 6% by weight of hydroxypropylcellulose (0.24 g as hydroxypropylcellulose) was added thereto. The mixture was granulated in a mortar, and the granules were passed through screen after drying in a shell dryer to yield granules of 30 mesh (500 μm) or less. Calcium stearate was mixed to the granules to be at 0.95%, and the mixture was compressed with a pressure of 500 kg using 7 mm diameter round-faced (9.5 R) punch to prepare tablets of the above composition.

REFERENCE EXAMPLE 4

| | |
|---|---|
| Active component | 22.0 mg |
| Lactose | 56.0 mg |
| Corn starch | 24.0 mg |
| Microcrystalline cellulose | 13.2 mg |
| Low substitued hydroxypropylcellulose | 8.0 mg |
| Hydroxypropylcellulose | 2.4 mg |
| Calcium stearate | 1.2 mg |
| [Total] | 126.8 mg |

After 5.6 g of lactose, 2.4 g of corn starch, 1.32 g of microcrystalline cellulose and 0.8 g of low substituted hydroxypropylcellulose (brand name; L-HPC/LH-11, produced by Shin-Etsu Chemical Co., Ltd.) were mixed with 2.2 g of dihydrate of calcium salt of the benzylsuccinic acid derivative represented by the formula (I) (active component), 4 g of an aqueous solution of 6% by weight of hydroxypropylcellulose (0.24 g as hydroxypropylcellulose) was added thereto. The mixture was granulated in a mortar, and the granules were passed through screen after drying in a shell dryer to yield granules of 30 mesh (500 μm) or less. Calcium stearate was mixed to the granules to be at 0.95%, and the mixtre was compressed with a pressure of 500 kg using 7 mm diameter round-faced (9.5 R) punch to prepare tablets of the above composition.

REFERENCE EXAMPLE 5

| | |
|---|---|
| Active component | 22.0 mg |
| Lactose | 56.0 mg |
| Corn starch | 24.0 mg |
| Microcrystalline cellulose | 13.2 mg |
| Low substitued hydroxypropylcellulose | 8.0 mg |
| Hydroxypropylcellulose | 2.4 mg |
| Calcium stearate | 1.2 mg |
| [Total] | 126.8 mg |

After 5.6 g of lactose, 2.4 g of corn starch, 1.32 g of microcrystalline cellulose and 0.8 g of Low substituted hydroxypropylcellulose (brand name; L-HPC/LH-22, produced by Shin-Etsu Chemical Co., Ltd.) were mixed with 2.2 g of dihydrate of calcium salt of the benzylsuccinic acid derivative represented by the formula (I) (active component), 4 g of an aqueous solution of 6% by weight of hydroxypropylcellulose (0.24 g as hydroxypropylcellulose) was added thereto. The mixture was granulated in a mortar, and the granules were passed through screen after drying in a shell dryer to yield granules of 30 mesh (500 μm) or less. Calcium stearate was mixed to the granules to be at 0.95%, and the mixture was copressed with a pressure of 500 kg using 7 mm diameter round-faced (9.5 R) punch to prepare tablets of the above composition.

REFERENCE EXAMPLE 6

| | |
|---|---|
| Active component | 22.0 mg |
| Lactose | 56.0 mg |
| Corn starch | 24.0 mg |
| Microcrystalline cellulose | 13.2 mg |
| Partly pregelatinized starch | 8.0 mg |
| Hydroxypropylcellulose | 2.4 mg |
| Calcium stearate | 1.2 mg |
| [Total] | 126.8 mg |

After 5.6 g of lactose, 2.4 g of corn starch, 1.32 g of microcrystalline cellulose, 0.8 g of partly pregelatinized starch (brand name: PCS [trademark], produced by Asahi Kasei Co., Ltd.), 0.24 g of hydroxypropylcellulose and 0.12 g of calcium stearate were mixed with 2.2 g of dihydrate of calcium salt of the benzylsuccinic acid derivative represented by the formula (I) (active component), the mixture was compressed with a pressure of 500 kg using 7 mm diameter round-faced (9.5 R) punch to prepare tablets of the above composition.

REFERENCE EXAMPLE 7

| | |
|---|---|
| Active component | 22.0 mg |
| Lactose | 56.0 mg |
| Corn starch | 24.0 mg |
| Microcrystalline cellulose | 13.2 mg |
| Sodium carboxymethyl starch | 8.0 mg |
| Hydroxypropylcellulose | 2.4 mg |
| Calcium stearate | 1.2 mg |
| [Total] | 126.8 mg |

After 5.6 g of lactose, 2.4 g of corn starch, 1.32 g of microcrystalline cellulose, 0.8 g of sodium carboxymethyl cellulose (brand name: Primogel [trademark], produced by Matsutani Chemical Co., Ltd.), 0.24 g of hydroxypropylcellulose and 1.2 g of calcium stearate were mixed with 2.2 g of dihydrate of calcium salt of the benzylsuccinic acid derivative represented by the formula (I) (active component), the mixture was compressed with a pressure of 500 kg using 7 mm diameter round-faced (9.5 R) punch to prepare tablets of the above composition.

REFERENCE EXAMPLE 8

| | |
|---|---|
| Active component | 22.0 mg |
| Lactose | 56.0 mg |
| Corn starch | 24.0 mg |
| Microcrystalline cellulose | 13.2 mg |
| Low substituted hydroxypropylcellulose | 8.0 mg |
| Hydroxypropylcellulose | 2.4 mg |
| Calcium stearate | 1.2 mg |
| [Total] | 126.8 mg |

After 5.6 g of lactose, 2.4 g of corn starch, 1.32 g of microcrystalline cellulose, 0.8 g of low substitued hydroxypropylcellulose (brand name; L--HPC/LH-11, produced by Shin-Etsu Chemical Co., Ltd.), 0.24 g of hydroxypropylcellulose and 0.12 g of calcium stearate were mixed with 2.2 g of dihydrate of calcium salt of the benzylsuccinic acid derivative represented by the formula (I) (active component), the mixture was compressed with a pressure of 500 kg using 7 mm diameter round-faced (9.5 R) punch to prepare tablets of the above composition.

REFERENCE EXAMPLE 9

| | |
|---|---|
| Active component | 22.0 mg |
| Lactose | 56.0 mg |
| Corn starch | 24.0 mg |
| Microcrystalline cellulose | 13.2 mg |
| Low substituted hydroxypropylcellulose | 8.0 mg |
| Hydroxypropylcellulose | 2.4 mg |
| Calcium stearate | 1.2 mg |
| [Total] | 126.8 mg |

After 5.6 g of lactose, 2.4 g of corn starch, 1.32 g of microcrystalline cellulose, 0.8 g of low substitued hydroxypropylcellulose (brand name; L-HPC/LH-22, produced by Shin-Etsu Chemical Co., Ltd.), 0.24 g of hydroxypropylcellulose and 0.12 g of calcium stearate were mixed with 2.2 g of dihydrate of calcium salt of the benzylsuccinic acid derivative represented by the formula (I) (active component), the mixture was compressed with a pressure of 500 kg using 7 mm diameter round-faced (9.5 R) punch to prepare tablets of the above composition.

EXAMPLE 1

| | |
|---|---|
| Active component | 5.0 mg |
| Microcrystalline cellulose | 27.5 mg |
| Lactose | 27.9 mg |
| Corn starch | 10.0 mg |
| Low substitued hydroxypropylcellulose | 3.0 mg |
| Calcium stearate | 0.8 mg |
| Light anhydrous silicic acid | 0.8 mg |
| [Total] | 75.0 mg |

After 275.0 g of microcrystalline cellulose, 279.0 g of lactose, 100.0 g of corn starch, 30.0 g of low substituted hydroxypropylcellulose (brand name: L-HPC/LH-11, produced by Shin-Etsu Chemical Co., Ltd.), 8.0 g of calcium stearate and 8.0 g of light anhydrous silicic acid (brand name: Adsolider [trademark] 101, produced by Freund Industrial Co., Ltd.) were mixed with 50.0 g of dihydrate of calcium salt of the benzylsuccinic acid derivative represented by the formula (I) (active component), the mixture was compressed with a pressure of about 700 kg by a tabletting machine using 6 mm diameter round-faced (5 R) punch to prepare tablets of the above composition.

EXAMPLE 2

| | |
|---|---|
| Active component | 5.0 mg |
| Microcrystalline cellulose | 27.5 mg |
| Lactose | 27.3 mg |
| Corn starch | 10.0 mg |
| Low substitued hydroxypropylcellulose | 3.0 mg |
| Calcium stearate | 0.8 mg |
| Light anhydrous silicic acid | 1.4 mg |
| [Total] | 75.0 mg |

After 275.0 g of microcrystalline cellulose, 273.0 g of lactose, 100.0 g of corn starch, 30.0 g of low substitued hydroxypropylcellulose (brand name: L-HPC/LH-11, produced by Shin-Etsu Chemical Co., Ltd.), 8.0 g of calcium stearate and 14.0 g of light anhydrous silicic acid (brand name: Adsolider [trademark] 101, produced by Freund Industrial Co., Ltd.) were mixed with 50.0 g of dihydrate of calcium salt of the benzylsuccinic acid derivative represented by the formula (I) (active component), the mixture was compressed with a pressure of about 700 kg by a tabletting machine using 6 mm diameter round-faced (5 R) punch to prepare tablets of the above composition.

EXAMPLE 3

| | |
|---|---|
| Active component | 22.0 mg |
| Lactate | 56.0 mg |
| Corn starch | 24.0 mg |
| Microcrystalline cellulose | 13.2 mg |
| Partly pregelatinized starch | 8.0 mg |
| Hydroxypropylcellulose | 2.4 mg |
| Calcium stearate | 1.2 mg |
| [Total] | 126.8 mg |

After 5.6 g of lactose, 2.4 g of corn starch, 1.32 g of microcrystalline cellulose and 0.8 g of partly pregelatinized starch (brand name: PCS [trademark], produced by Asahi Kasei Co., Ltd.) were mixed with 2.2 g of dihydrate of calcium salt of the benzylsuccinic acid derivative represented by the formula (I) (active component), 4 g of an aqueous solution of 6% by weight of hydroxypropylcellulose (0.24 g as hydroxypropylcellulose) was added thereto. The mixture was granulated in a mortar, and the granules were passed through screen after drying in a shell dryer to yield granules of 30 mesh (500 μm) or less. Calcium stearate was mixed to the granules to be at 0.95%, and the mixture was compressed with a pressure of 500 kg using 7 mm diameter round-faced (9.5 R) punch to prepare tablets of the above composition.

EXAMPLE 4

| | |
|---|---|
| Active component | 22.0 mg |
| Lactose | 60.7 mg |
| Corn starch | 26.0 mg |
| Microcrystalline cellulose | 13.2 mg |
| Light anhydrous silicic acid | 1.3 mg |
| Hydroxypropylcellulose | 2.4 mg |
| Calcium stearate | 1.2 mg |
| [Total] | 126.8 mg |

After 6.07 g of lactose, 2.6 g of corn starch, 1.32 g of microcrystalline cellulose and 0.13 g of light anhydrous silicic acid (brand name: Adsolider [trademark] 101, produced by Freund Industrial Co., Ltd.) were mixed with 2.2 g of dihydrate of calcium salt of the benzylsuccinic acid derivative represented by the formula (I) (active component), 4 g of an aqueous solution of 6% by weight of hydroxypropylcellulose (0.24 g as hydroxypropylcellulose) was added thereto. The mixture was granulated in a mortar, and the granules were passed through screen after drying in a shell dryer to yield granules of 30 mesh (500 μm) or less. Calcium stearate was mixed to the granules to be at 0.95%, and the mixture was compressed with a pressure of 500 kg using 7 mm diameter round-faced (9.5 R) punch to prepare tablets of the above composition.

EXAMPLE 5

| | |
|---|---|
| Active component | 22.0 mg |
| Lactose | 54.7 mg |
| Corn starch | 24.0 mg |
| Microcrystalline cellulose | 13.2 mg |
| Partly pregelatinized starch | 8.0 mg |
| Light anhydrous silicic acid | 1.3 mg |
| Hydroxypropylcellulose | 2.4 mg |
| Calcium stearate | 1.2 mg |
| [Total] | 126.8 mg |

After 5.47 g of lactose, 2.4 g of corn starch, 1.32 g of microcrystalline cellulose, 0.8 g of partly pregelatinized starch (brand name: PCS [trademark], produced by Asahi Kasei Co., Ltd) and 0.13 g of light anhydrous silicic acid (brand name: Adsolider [trademark] 101, produced by Freund Industrial Co., Ltd.) were mixed with 2.2 g of dihydrate of calcium salt of the benzylsuccinic acid derivative represented by the formula (I) (active component), 4 g of an aqueous solution of 6% by weight of hydroxypropylcellulose (0.24 g as hydroxypropylcellulose) was added thereto. The mixture was granulated in a mortar, and the granules were passed through screen after drying in a shell dryer to yield granules of 30 mesh (500 μm) or less. Calcium stearate was mixed to the granules to be at 0.95%, and the mixture was compressed with a pressure of 500 kg using 7 mm diameter round-faced (9.5 R) punch to prepare tablets of the above composition.

EXAMPLE 6

| | |
|---|---|
| Active component | 22.0 mg |
| Lactose | 56.9 mg |
| Corn starch | 24.4 mg |
| Microcrystalline cellulose | 14.0 mg |
| Partly pregelatinized starch | 9.0 mg |
| Hydroxypropylcellulose | 2.5 mg |
| Calcium stearate | 1.2 mg |
| [Total] | 130.0 mg |

After 569 g of lactose, 244 g of corn starch, 140 g of microcrystalline cellulose and 90 g of partly gelatinized starch (brand name: PCS [trademark], Asahi Kasei Co., Ltd) were mixed with 2.2 g of dihydrate of calcium salt of the benzylsuccinic acid derivative represented by the formula (I) (active component), 416.7 g of an aqueous solution of 6% by weight of hydroxypropylcellulose (25 g as hydroxypropylcellulose) was added thereto. The mixture was granulated in a high shear mixer. The granules were dried using a fluidized-bed dryer and passed through screen to yield granules of 30 mesh (50 μm) or less. Calcium stearate was mixed to the granules to be at 0.92%, and the mixture was tabletted by a tabletting machine with a pressure of 500 kg using 7 mm diameter round-faced (9.5 R) punch to prepare tablets of the above composition.

TEST EXAMPLE 1

Dissolution Test (1)

For the tablets described in Examples 1 and 2 and Reference Example 1, the dissolution test (a quantitative method: HPLC, a detection wave length: 220 nm) was carried out using 900 mL of first fluid of the Japanese Pharmacopoeia at 50 rpm according to the paddle method, apparatus 2 of the dissolution test methods of the 13th revised Japanese Pharmacopoeia. From the results of these dissolution tests as shown in FIG. 1, the tablets of Examples 1 and 2 showed much more excellent dissolution than those of Reference Example 1.

TEST EXAMPLE 2

Dissolution Test (2)

Figure 2:
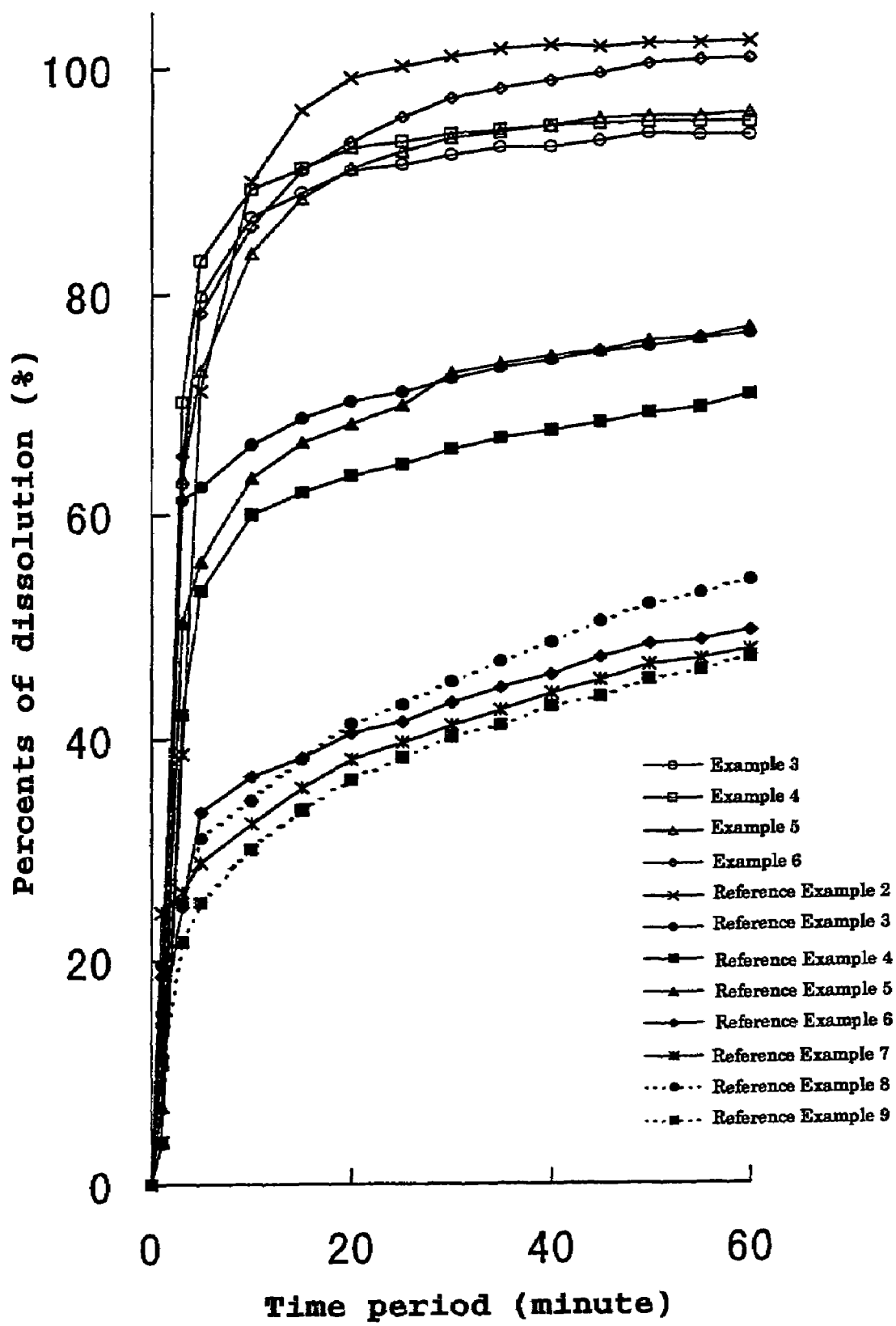
FIG. 2 is a graph showing a dissolution of various tablets described in Examples 3 to 6 and in Reference Examples 2 to 9 in which dihydrate of calcium salt of the benzylsuccinic acid derivative of the above formula (I) is an active ingredient. The vertical and the horizontal axes denote percents of dissolution (%) of the active ingredient and time periods (minute) passed after the start of the tests, respectively.

For the tablets described in Examples 3 to 6 and Reference Examples 2 to 9, the dissolution test (a quantitative method: UV absorbance determination, a detection wave length: 205 nm) was carried out using 900 mL of first fluid of the Japanese Pharmacopoeia at 50 rpm according to the paddle method, apparatus 2 of the dissolution test methods of the 13th revised Japanese Pharmacopoeia. From the results of these dissolution tests as shown in FIG. 2, the tablets of Examples 3 to 6 showed much more excellent dissolution than those of Reference Example 3 to 9.

TEST EXAMPLE 3

Compatibility Test

One gram of each of the following various additives was mixed with 1 g of dihydrate of calcium salt of the benzylsuccinic acid derivative represented by the formula (I), and the mixture was placed for two weeks under a condition of temperature at 60° C. and relative humidity of 80%. Then its appearance was observed.

Additives:

Partly pregelatinized starch (brand name: PCS [trademark], produced by Asahi Kasei Co., Ltd)

Carmellose (brand name: NS-300 [trademark], produced by Gotoku Yakuhin Co., Ltd)

Carmellose calcium (brand name: ECG-505 [trademark], produced by Gotoku Yakuhin Co., Ltd)

Croscarmellose sodium (brand name: Ac-Di-Sol, produced by Asahi Kasei Co., Ltd)

Light anhydrous Silicic acid (brand name: Adsolider [trademark] 101, Freund Industrial Co., Ltd.)

The results are shown in the following Table 1. The dihydrate of calcium salt of the benzylsuccinic acid derivative represented by the formula (I) was stable in combination with partly pregelatinized starch or light anhydrous silicic acid, but caused an incompatible combination with carmellose, carmellose calcium or croscarmellose sodium.

TABLE 1

| Additives | Appearance |
| --- | --- |
| Partly pregelatinized starch | No change |
| Carmellose | Colored with pale yellow |
| Carmellose calcium | Colored with faint yellow |
| Croscarmellose sodium | Colored with faint yellow |
| Light anhydrous silicic acid | No change |

TEST EXAMPLE 4

Stability Test

The tablets described in Example 3 and 4 and Reference Example 2 were placed for 1 week under a condition of temperature at 60° C. and relative humidity of 80%, and then appearance of the tablets, amounts of their decompositions and dissolution time periods using first fluid of the Japanese Pharmacopoeia were examined. As the results, the tablets described in Reference Example 2 containing carmellose changed a color of appearance into faint yellow indicating an increase of decompositions. However, the tablets described in Examples 3 and 4 using respectively partly pregelatinized starch and light anhydrous silicic acid did not detect any changes, and their dissolution time periods did not change and consequently the tablets were extremely stable.

The invention claimed is:

1. A method for controlling release of an active ingredient from an oral pharmaceutical composition comprising:
    combining said active ingredient with a disintegrating agent and diluents,
    wherein said active ingredient comprises a calcium salt of a benzylsuccinic acid represented by the formula:

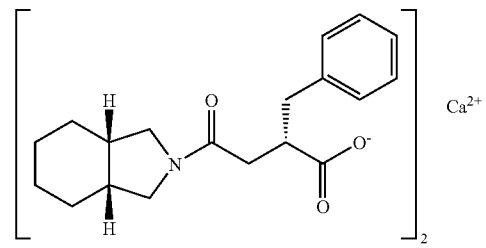

or its hydrate,
    wherein said disintegrating agent comprises at least one member selected from the group consisting of silicon dioxide and partly pregelatinized starch,
    and wherein said diluents comprise (a) microcrystalline cellulose, (b) lactose and (c) corn starch,
    and wherein disintegration of the pharmaceutical composition and dissolution of the active ingredient are sufficient so that 75% or more of said active ingredient releases in human gastric juice within 20 minutes of administering said oral composition.

2. The method of claim 1, wherein said disintegrating agent is silicon dioxide.

3. The method of claim 1, wherein said disintegrating agent is partly pregelatinized starch.

4. The method of claim 2, wherein said silicon dioxide is present in an amount of 0.5 to 5% by weight based on the total weight of said composition.

5. The method of claim 3, wherein said partly pregelatinized starch is present in an amount of 5 to 20% by weight based on the total weight of said composition.

* * * * *